United States Patent
Walkley et al.

(10) Patent No.: US 6,683,076 B2
(45) Date of Patent: Jan. 27, 2004

(54) METHODS FOR THERAPEUTIC USE OF GLUCOSYLCERAMIDE SYNTHESIS INHIBITORS AND COMPOSITION THEREOF

(75) Inventors: Steven Walkley, Bronx, NY (US); Gordon D. Holt, Gaithersburg, MD (US)

(73) Assignee: Oxford Glyco-Sciences (UK) Ltd, Abingdon (GB)

( * ) Notice: Subject to any disclaimer, the term of this patent is extended or adjusted under 35 U.S.C. 154(b) by 157 days.

(21) Appl. No.: 10/007,306

(22) Filed: Oct. 19, 2001

(65) Prior Publication Data

US 2002/0115667 A1 Aug. 22, 2002

Related U.S. Application Data

(63) Continuation of application No. PCT/GB00/01563, filed on Apr. 20, 2000.

(51) Int. Cl.⁷ .............................................. A61K 31/54
(52) U.S. Cl. .................................................... 514/222.2
(58) Field of Search ....................... 514/222.2

(56) References Cited

U.S. PATENT DOCUMENTS

| | | | |
|---|---|---|---|
| 5,798,366 A | | 8/1998 | Platt et al. |
| 6,426,198 B1 | * | 7/2002 | Carstea et al. ............ 435/69.1 |
| 6,495,570 B2 | * | 12/2002 | Jacob et al. ................ 514/328 |
| 2001/0044453 A1 | * | 11/2001 | Jacob et al. ................ 514/328 |

FOREIGN PATENT DOCUMENTS

WO    WO 98/02161    1/1998

OTHER PUBLICATIONS

Liu et al., "Alleviation of Neuronal Ganglioside Storage Does Not Improve the Clinical Course of Niemann–Pick C Disease Mouse" (2000) Human Molec. Genet., 9(7), 1087–1092.*

Cruz et al., "Fate of Endogenously Synthesized Cholesterol in Niemann–Pick Type C1 Cells" (2000) J. Biol. Chem., 275(52), 41309–41316.*

Ory, D.S., "Niemann–Pick Type C: A Disorder of Cellular Cholesterol Trafficking" (2000) Biochim. Biophys. Acta, 1529, 331–339.*

Beers et al., "The Merck Manual of Diagnosis and Therapy Seventeenth Edition", Merck Research Laboratories, New York, Chapter 16, pp. 212–216 (1999).

Platt et al., Biochemical Pharmacology, GB, Pergamon, Oxford, 56:421–430 (1998).

Platt et al., Journal of Biological Chemistry, 269:27108–27114 (1994).

Platt et al., Science, US, American Association for the Advancement of Science, 276:428–431 (1997).

Meuillet et al., Experimental Cell Research, 256:74–82 (2000).

Rösner, Annals of the New York Academy of Sciences, 845:200–214 (1998).

Zervas et al., Current Biology, 11:1283–1287 (2001).

* cited by examiner

*Primary Examiner*—Jon P Weber
(74) *Attorney, Agent, or Firm*—Klauber & Jackson

(57) ABSTRACT

Methods for treatment of disorders associated with glycolipid accumulation, such as Niemann-Pick Type C (NPC) disease, comprising administering a therapeutically effective amount of an inhibitor of glucosylceramide synthesis. Inhibitors of glucosylceramide synthesis include N-butyldeoxynojirimycin, N-butyldeoxygalactonojirimycin, and N-nonyldeoxynojirimycin; 1-phenyl-2-decanoylamino-3-morpholino-1-propanol (PDMP), D-threo-1-phenyl-2-decanoylamino-3-morpholino-1-propanol and structurally related analogues thereof; and agents capable of increasing the rate of neuronal glycolipid degradation.

5 Claims, 1 Drawing Sheet

METHODS FOR THERAPEUTIC USE OF GLUCOSYLCERAMIDE SYNTHESIS INHIBITORS AND COMPOSITION THEREOF

RELATED PATENT APPLICATIONS

This application is a continuation of PCT/GB00/01563 filed Apr. 20, 2000, which application is herein specifically incorporated by reference.

INTRODUCTION

The present invention relates to therapeutic methods for treatment of conditions related to glucosylceramide synthesis disorders, for example, Niemann-Pick C storage disease, Alzheimer's disease, epilepsy, stroke, and Parkinson's disease.

BACKGROUND OF THE INVENTION

Niemann-Pick Type C (NPC) disease, also known as Niemann-Pick disease with cholesterol esterification block, is an autosomal recessive storage disorder of cholesterol metabolism. NPC patients generally appear normal for the first few years of life. However, organomagly of the liver and spleen soon emerge, and may result in jaundice or other symptoms of dysfunction. NPC patients also gradually develop neurologic abnormalities such as ataxia, tremors, seizures, and loss of speech, cognitive and motor skills, and difficulty with upward and downward eye movements. Impairment progresses, particularly resulting from increasing neural degeneration, and death usually occurs by 5–15 years of age.

Vanier et al. (1991) reported that Niemann-Pick Type C is heterogeneous, suggesting the possibility that more than one genetic mutation gives rise to the disease. Molecular studies recently substantiated this possibility. A gene most commonly mutated in Niemann-Pick Type C patients has been identified as NPC1 and mapped to 18q11–q12. The NPC1 gene encodes a protein of 1,278 amino acids, and bears some sequence homology to the putative sterol-sensing regions of SREBP cleavage-activating protein and 3-hydroxy-3-methylglutaryl coenzyme A reductase. A specific function for the NPC1 gene product is unknown at this time, although biochemical studies are suggestive that NPC1 gene mutations somehow disturbs cholesterol metabolism. For example, NPC cells are blocked in cholesterol esterification and do not effectively translocate cholesterol from lysosomes to other intracellular organelles.

Evidence for a second possible gene mutated in Niemann-Pick type C has been described, although it has not yet been identified. Patients with NPC1 mutations have been subclassified as having Niemann-Pick type C1 disease, while patients with other mutated gene(s) as having Niemann-Pick type C2 disease. There is no known difference between the clinical courses of type C1 and C2 patients, which appear to respond in the same way to disease treatments. In addition, the C1I/C2 subclassification is not universally applied. Therefore, Niemann-Pick Type C diseases originating from NPC1 or other gene mutations are collectively referred to as NPC here.

Biochemical findings for NPC patients show a marked accumulation of cholesterol in the liver and spleen, as well as elevated sphingomyelin levels. However, sphingomyelinase activity remains normal in these tissues. This finding distinguishes NPC from Niemann-Pick Types A and B diseases which are caused by lysosomal sphingomyelinase mutations, and exhibit markedly reduced levels of this enzyme.

In addition to the liver and the spleen, other cells of NPC patients store cholesterol as well. For example, bone marrow cells take on a characteristic foamy appearance due to the presence of large numbers of storage inclusions, while eye and skin cells typically are less affected. Neuronal cells store some cholesterol, although glycolipid accumulation predominates, particularly $G_{M2}$ ganglioside. Affected neuronal cells in NPC patients undergo morphologic changes including the development of fibrillar tangles that are structurally similar to those seen in neurodegenerative disorders such as Alzheimer's disease and tuberous sclerosis. The age of onset and the rapidity of neuronal deterioration in NPC patients can vary considerably. The mechanism underlying these neurologic changes is unknown. It has been proposed that elevated levels of $G_{M2}$ may induce ectopic dendritic proliferation and meganeurite formation (Goodman and Walkley (1996) Brain Res Dev Brain Res 93:162–71). Dendritogenesis and neuron changes correlate well with disease severity in a feline model of NPC (March et al, 1997) Acta Neuropathol. 94:164–172).

There is as yet no accepted treatment for NPC disease. Given the observations supporting the origin of NPC disease in a cholesterol metabolism defect, most treatment attempts have focused on reducing cholesterol storage (Sylvain et al. (1994) Pediatr. Neurol. 10:228–32; Patterson et al (1993) Neurology 43:61–4). However, restricting cholesterol intake or treating patients with a range of cholesterol-lowering drugs has had puzzlingly little effect on the tissue storage levels of this material, and no apparent effect on the disease's progress.

It is generally accepted that the glycolipid accumulation component of NPC disease is a secondary effect of the cholesterol metabolism defect component (see for example Chapter 85 in The Metabolic and Molecular Bases of Inherited Disease, $7^{th}$ edition, McGraw-Hill Inc, New York, pp 2625–2639 (1995), Loftus et al. (1997) Science 277: 232–235). Thus, until now, little attention has focused on treating this component of the disease.

SUMMARY OF THE INVENTION

The imino sugar N-butyldeoxynojirimycin (NB-DNJ) is a potent inhibitor of alpha-glucosidase 1, an enzyme involved in N-glycan synthesis, and an even more potent inhibitor of glucosylceramide glucosyltransferase. NB-DNJ is currently undergoing clinical trials as a treatment for Gaucher and Fabry diseases, which are glycolipid storage disorders resulting from mutations in glucocerebrosidase and alpha-galactosidase A, respectively (see FIG. 1). The rationale underlying these clinical trials is based on the observation that cells treated with NB-DNJ produce markedly reduced glucosylceramide levels because of inhibition of glucosylceramide synthesis. Thus, the clinical trials are determining whether patient health benefits could be achieved by balancing a NB-DNJ induced decrease in the rate of glucosylceramide synthesis against the impaired rate of glycolipid clearance seen in Gaucher and Fabry disease patients. Methods and processes for the production of N-butyldeoxynojirimycin can be found for example in U.S. Pat. Nos. 4,182,767, 4,266,025, and 5,151,519; as well as EP-B-0012278 and EP-A-0624652, which publications are herein specifically incorporated by reference.

The present invention is based in part on the discovery that neuronal glycolipid storage seen in NPC patients is reduced by NB-DNJ treatment. As demonstrated in the experiments described below, NB-DNJ markedly reduces clinical and pathological symptoms in feline and murine models of NPC.

Accordingly, in a first aspect, the present invention provides a method of treating Niemann-Pick type C disease, comprising administering a therapeutically effective amount of an inhibitor of glucosylceramide synthesis. In one embodiment, the inhibitor is an imide sugar. In more specific embodiments, the imide sugar is N-butyldeoxynojirimycin, N-butyldeoxygalactonojirimycin, or N-nonyldeoxynojirimycin. In a more specific embodiment, the imide sugar is N-butyldeoxynojirimycin, which is a potent inhibitor of both alpha-glucosidase 1 and glucosylceramide glucosyltransferase. In another embodiment, the inhibitor of glucosylceramide synthesis is 1-phenyl-2-decanoylamino-3-morpholino-1-propanol (PDMP), D-threo-1-phenyl-2-decanoylamino-3-morpholino-1-propanol and structurally related analogues thereof.

In another embodiment of the method of the invention, a nucleic acid encoding a peptide or protein inhibitor of glucosylceramide synthesis is administered, and in a related embodiment, an antisense sequence or catalytic RNA capable of interfering with the expression of an enzyme required for glucosylceramide synthesis (e.g. glucosylceramide synthase) is administered. In further embodiments, inhibition of glucosylceramide synthesis is achieved with a combination of these approaches, for example, administration of an imide sugar and an antisense molecule capable of interfering with the expression of an enzyme involved in glucosylceramide synthesis.

In a second aspect, the present invention provides a pharmaceutical composition comprising an inhibitor of glucosylceramide synthesis selected from the group of N-butyldeoxynojirimycin, N-butyldeoxygalactonojirimycin, N-nonyldeoxynojirimycin, 1-phenyl-2-decanoylamino-3-moipholino-1-propanol (PDMP), D-threo-1-phenyl-2-decanoylamino-3-morpholino-1-propanol, and structurally related analogues thereof, and a pharmaceutically acceptable carrier.

In a third aspect, the invention provides a method of treating Niemann-Pick type C disease, comprising administering a therapeutically effective amount of an agent capable of increasing the rate of neuronal glycolipid degradation. In more specific embodiments, the agent is a neuronal glycolipid degrading enzyme, for example, a lysosomal hexoseaminidase, a galactosidase, a sialidase and glucosylceramide glucosidase. In further embodiments, the agent is a molecule which increases the activity of a glycolipid degrading enzyme. In still further embodiments, the agent is a nucleic acid sequence (DNA or RNA) which encodes a neuronal glycolipid degrading enzyme.

In a fourth aspect, the present invention provides a method of treating Alzheimer's disease, comprising administering a therapeutically effective amount of an inhibitor of glucosylceramide synthesis. In one embodiment, the inhibitor of glucosylceramide synthesis is an imino sugar. In more specific embodiments, the imide sugar is N-butyldeoxynojirimycin, N-butyldeoxygalactonojirimycin, or N-nonyldeoxynojirimycin. In a more specific embodiment, the imide sugar is N-butyldeoxynojirimycin, which is a potent inhibitor of both alpha-glucosidase 1 and glucosylceramide glucosyltransferase. In another embodiment, the inhibitor of glucosylceramide synthesis is 1-phenyl-2-decanoylamino-3-morpholino-1-propanol (PDMP), D-threo-1-phenyl-2-decanoylamino-3-morpholino-1-propanol and structurally related analogues thereof.

In a fifth aspect, the invention provides a method of treating Alzheimer's disease, comprising administering a therapeutically effective amount of an agent capable of increasing the rate of neuronal glycolipid degradation. In more specific embodiments, the agent is a neuronal glycolipid degrading enzyme, for example, a lysosomal hexoseaminidase, a galactosidase, a sialidase and glucosylceramide glucosidase. In further embodiments, the agent is a molecule which increases the activity of a glycolipid degrading enzyme. In still further embodiments, the agent is a nucleic acid sequence (DNA or RNA) which encodes a neuronal glycolipid degrading enzyme.

In a sixth aspect, the present invention provides a method of treating or ameliorating epilepsy, comprising administering a therapeutically effective amount of an inhibitor of glucosylceramide synthesis. In one embodiment, the inhibitor of glucosylceramide synthesis is an imino sugar. In more specific embodiments, the imide sugar is N-butyldeoxynojirimycin, N-butyldeoxygalactonojirimycin, or N-nonyldeoxynojirimycin. In a more specific embodiment, the imide sugar is N-butyldeoxynojirimycin, which is a potent inhibitor of both alpha-glucosidase 1 and glucosylceramide glucosyltransferase. In another embodiment, the inhibitor of glucosylceramide synthesis is 1-phenyl-2-decanoylamino-3-morpholino-1-propanol (PDMP), D-threo-1-phenyl-2-decanoylamino-3-morpholino-1-propanol and structurally related analogues thereof.

In a seventh aspect, the invention provides a method of treating or ameliorating epilepsy, comprising administering a therapeutically effective amount of an agent capable of increasing the rate of neuronal glycolipid degradation. In more specific embodiments, the agent is a neuronal glycolipid degrading enzyme, for example, a lysosomal hexoseaminidase, a galactosidase, a sialidase and glucosylceramide glucosidase. In further embodiments, the agent is a molecule which increases the activity of a glycolipid degrading enzyme. In still further embodiments, the agent is a nucleic acid sequence (DNA or RNA) which encodes a neuronal glycolipid degrading enzyme.

Preliminary clinical trials have shown that neurodegenerative processes seen with Parkinson's disease, stroke and spinal cord injuries seem to improve by treating patients with GM1 ganglioside (Alter (1998) Ann N Y Acad Sci 845:391–4011; Schneider (1998) Ann N Y Acad Sci 845:363–73; Geisler (1998) Ann N Y Acad Sci 845: 374–81). Accordingly, in a separate eighth aspect, the invention features a method of modulating glucosylceramide synthesis in Parkinson's disease, stroke, and spinal cord injuries, comprising administering a therapeutically effective amount of a ganglioside. In a specific embodiment, the ganglioside is GM1 ganglioside.

In a ninth aspect, the invention features a pharmaceutical composition comprising a ganglioside, useful for treatment of Parkinson's disease, stroke, and spinal cord injuries, and a pharmaceutically acceptable carrier. In a more specific embodiment, the ganglioside is GM1 ganglioside.

In another embodiment, the pharmaceutical composition comprises an inhibitor of glucosylceramide synthesis and a ganglioside, useful for simultaneous, sequential or separate treatment in the treatment of a condition treatable by the administration of a ganglioside. In a more specific embodiment, the ganglioside is GM1 ganglioside. In one embodiment, the glucosylceramide synthesis inhibitor is an imino sugar. In more specific embodiments, the imide sugar is N-butyldeoxynojirimycin, N-butyldeoxygalactonojirimycin, or N-nonyldeoxynojirimycin. In another embodiment, the inhibitor of glucosylceramide synthesis is 1-phenyl-2-decanoylamino-3-morpholino-1-propanol (PDMP), D-threo-1-phenyl-2-decanoylamino-3-morpholino-1-propanol and structurally related analogues thereof.

In another embodiment, the pharmaceutical composition comprises a therapeutically effective amount of an agent capable of increasing the rate of neuronal glycolipid degradation and a ganglioside. In a more specific embodiment, the ganglioside is GM1 ganglioside. In other specific embodiments, the agent is a neuronal glycolipid degrading enzyme, for example, a lysosomal hexoseaminidase, a galactosidase, a sialidase and glucosylceramide glucosidase. In further embodiments, the agent is a molecule which increases the activity of a glycolipid degrading enzyme. In still further embodiments, the agent is a nucleic acid sequence (DNA or RNA) which encodes a neuronal glycolipid degrading enzyme.

Other objects and advantages will become apparent from a review of the ensuing detailed description taken in conjunction with the following illustrative drawing.

DETAILED DESCRIPTION OF THE INVENTION

Figure 1:
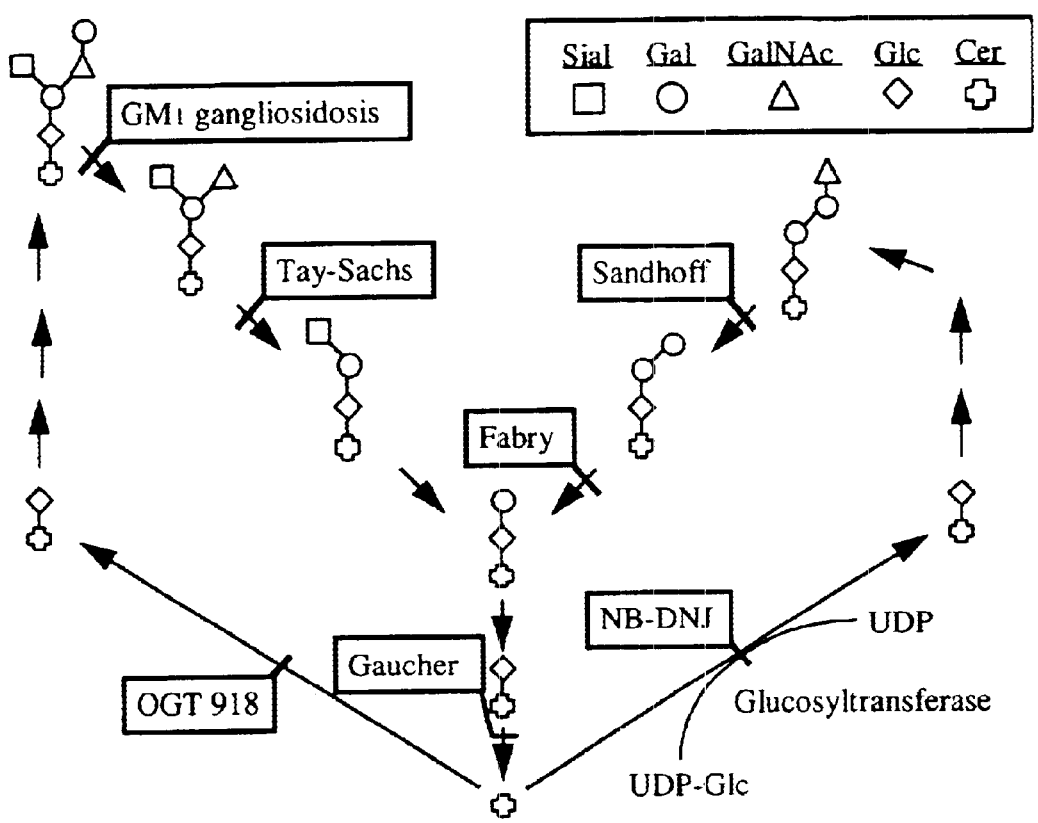
FIG. 1 is a schematic representation of the synthesis and degradation of glucosylceramide-containing glycolipids. Examples of genetic diseases resulting from a defect in one of the enzymes required for glycolipid degradation are indicated. The enzyme reaction inhibited by N-butyldeoxynojirimycin to decrease the synthesis of glucosylceramide-containing glycolipids is also shown.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "an inhibitor of glucosylceramide synthesis" includes mixtures of such inhibitors, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

In the context of the present invention, the term "inhibitor" of glycolipid synthesis is, more specifically, an inhibitor of glucosylceramide synthesis, and includes molecules such as N-butyldeoxynojirimycin, N-butyldeoxygalactonojirimycin, N-nonyldeoxynojirimycin and other imino sugar-structured inhibitors of glucosylceramide synthesis. Also included are agents such as 1-phenyl-2-decanoylamino-3-morpholino-1-propanol (PDMP), D-threo-1-phenyl-2-decanoylamino-3-morpholino-1-propanol and structurally related analogues thereof which exhibit the ability to inhibit glucosylceramide synthesis.

Furthermore, inhibition can also be achieved by the use of genetic approaches, based on the introduction of nucleic acid coding for proteins or peptides capable of inhibiting glucosylceramide synthesis or antisense sequences or catalytic RNA capable of interfering with the expression of enzymes responsible for glucosylceramide synthesis (e.g. glucosylceramide synthase). A combination of any of the above approaches can be used.

The term "substantially pure," when referring to a polypeptide, means a polypeptide that is at least 60%, by weight, free from the proteins and naturally-occurring organic molecules with which it is naturally associated. A substantially pure glucosylceramide synthesis inhibitor is at least 75%, more preferably at least 90%, and most preferably at least 99%, by weight, glucosylceramide synthesis inhibitor. A substantially pure glucosylceramie synthesis inhibitor such as N-butyldeoxynojirimycin (NB-DNJ), can be obtained, for example, by chemical synthesis or by isolation from natural sources. Purity can be measured by any appropriate method, e.g., column chromatography, polyacrylamide gel electrophoresis, or HPLC analysis.

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount of a reagent sufficient to achieve the desired treatment effect.

GENERAL ASPECTS OF THE INVENTION

Niemann-Pick Type C (NPC) disease is a disease associated with cholesterol and accumulation in the liver, spleen, bone marrow, as well as glycolipid accumulation in neuronal cells. Morphological changes in affected neuronal cells include the development of fibrillar tangles similar to those seen in neurodegenerative disorders such as Alzheimer's disease and tuberous sclerosis. The mechanism underlying these neurologic changes is unknown. Disorders of lipid metabolism also appear to play a critical role in such diseases as Alzheimer's disease and epilepsy. Accordingly, this invention features a new method of treating NPC, Alzheimer's disease, and epilepsy, by administering an inhibitor of glycolipid synthesis. The experiments described below support the effect of inhibitors of GM1 synthesis, such as NB-DNJ, on animal models of NPC.

By contrast, preliminary clinical trials have shown that neurodegenerative processes seen with Parkinson's disease, stroke and spinal cord injuries seem to improve by treating patients with GM1 ganglioside (Alter (1998) Ann N Y Acad Sci 845:391–4011; Schneider (1998) Ann N Y Acad Sci 845:363–73; Geisler (1998) Ann N Y Acad Sci 845: 374–81). Accordingly, co-administration of glucosylceramide synthesis inhibitors with GMI ganglioside would provide the clinician greater control over this treatment course. Inhibitors like NB-DNJ would limit patient-specific inconsistencies by blocking their neuronal glycolipid synthesis. In addition, inhibiting glucosylceramide synthesis would limit the metabolism of administered glycolipids into other, perhaps unproductive, forms. Thus, the ability to modulate or control glucosylceramide synthesis with inhibitors such as NB-DNJ is believed to be useful is treatment of a wide variety of neuronal disorders.

Pharmaceutical Compositions and Methods of Administration

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection by aerosol inhaler.

In another embodiment, the compound can be delivered in a vesicle, in particular a liposome (see Langer (1990) Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115–138). Other suitable controlled release systems are discussed in the review by Langer (1990) Science 249:1527–1533.

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of NPC and related disorders can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Therapeutic Uses of Glucosylceramide Synthesis Inhibitors

The invention provides for treatment or prevention of glucosylceramide synthesis-related diseases and disorders, such as NPC, Alzheimer's disease, and epilepsy, by administration of a therapeutic agent capable of inhibiting glucosylceramide synthesis. Such agents include but are not limited to: imide sugars such as N-butyldeoxynojirimycin, N-butyldeoxygalactonojirimycin, and N-nonyldeoxynojirimycin; compounds such as 1-phenyl-2-decanoylamino-3-morpholino-1-propanol (DMP), D-threo-1-phenyl-2-decanoylamino-3-morpholino-1-propanol and structurally related analogues thereof; nucleic acids encoding a peptide or protein inhibitor of glucosylcennide synthesis; an antisense sequence or catalytic RNA capable of interfering with the expression of one or more enzymes required for glucosylceramide synthesis, such as, glucosylceramide synthase.

The change in gluycosylceramide synthesis due to the administration of such compounds can be readily detected, e.g., by obtaining a biopsy sample, or by assaying in vitro the levels of activities of enzymes involved in glucosylceramide synthesis, or the levels of mRNAs encoding such enzymes, or any combination of the foregoing. Such assays can be performed before and after the administration of the compound as described herein.

In one embodiment, a nucleic acid comprising a sequence encoding a peptide or protein inhibitor of glucosylceramide synthesis is administered. In another embodiment, a nucleic acid sequence encoding an agent capable of increasing the rate of neuronal glycolipid degradation, e.g., a glucosylceramide glucosidase, is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488–505; Wu and Wu (1991) Biotherapy 3:87–95; Tolstoshev (1993) Ann. Rev. Pharmacol. Toxicol. 32:573–596; Mulligan (1993) Science 260:926–932; and Morgan and Anderson (1993) Ann. Rev. Biochem. 62:191–217; May (1993) TIBTECH 11(5): 155–215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspects, the compound comprises a nucleic acid encoding a peptide or protein inhibitor of glucosylceramide synthesis or encoding an enzyme required for neuronal glycolipid degradation, such nucleic acid being part of an expression vector that expresses a the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932–8935; Zijlstra et al. (1989) Nature 342:435–438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated April 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al. (1989) Nature 342:435–438).

In a further embodiment, a viral vector that contains a nucleic acid encoding a glycolipid degrading enzyme is used, for example, a retroviral vector can be used (see Miller et al. (1993) Meth. Enzymol. 217:581–599). These retroviral vectors have been modified to delete retroviral sequences that are not necessary for packaging of the viral genome and integration into host cell DNA. The nucleic acid encoding the enzyme to be used in gene therapy is cloned into the vector, which facilitates delivery of the gene into a subject. More detail about retroviral vectors can be found in Boesen et al. (1994) Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are:, Clowes et al. (1994) J. Clin. Invest. 93:644–651; Kiem et al. (1994) Blood 83:1467–1473; Salmons and Gunzberg (1993) Human Gene Therapy 4:129–141; and Grossman and Wilson (1993) Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499–503 present a review of adenovirus-based gene therapy. Bout et al. (1994) Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al. (1991) Science 252:431–434; Rosenfeld et al. (1992) Cell 68:143–155; Mastrangeli et al. (1993) J. Clin. Invest. 91:225–234; PCT Publication WO94/12649; and Wang, et al. (1995) Gene Therapy 2:775–783. Adeno-associated virus (AAV) has also been proposed for use in gene therapy (Walsh et al. (1993) Proc. Soc. Exp. Biol. Med. 204:289–300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599–618; Cohen et al. (1993) Meth. Enzymol. 217:618–644; Cline (1985) Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In an embodiment in which recombinant cells are used in gene therapy, a nucleic acid encoding a peptide or protein inhibitor of glucosylceramide synthesis, or an agent capable of increasing the rate of neuronal glycolipid degradation is introduced into the cells such that it is expressible by the cells or their progeny, and the recombinant cells are then administered in vivo for therapeutic effect. In a specific embodiment, stem or progenitor cells are used. Any stem or progenitor cells which can be isolated and maintained in vitro can be used in accordance with this embodiment of the present invention (see e.g. PCT Publication WO 94/08598, dated Apr. 28, 1994; Stemple and Anderson (1992) Cell 71:973–985; Rheinwald (1980) Meth. Cell Bio. 21A:229; and Pittelkow and Scott (1986) Mayo Clinic Proc. 61:771).

In another embodiment, the nucleic acid to be introduced for purposes of gene therapy may comprise an inducible promoter operably linked to the coding region, such that expression of the nucleic acid is controllable by controlling the presence or absence of the appropriate inducer of transcription.

Direct injection of a DNA coding for a peptide or protein inhibitor of glucosylceramide synthesis or an agent capable of increasing the rate of neuronal glycolipid degradation may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection and the elicitation of an immune response in the subject to the protein encoded by the injected DNA.

In one embodiment of the invention, NPC is treated or prevented by administration of a compound that inhibits the expression of one or more enzymes responsible for glucosylceramide synthesis. Compounds useful for this purpose may include antibodies directed to glucosylceramide synthesis enzymes (and fragments and derivatives containing the binding region thereof), and antisense or ribozyme nucleic acids.

In a further embodiment, the expression of an enzyme involved in neuronal glucosylceramide synthesis is inhibited by use of antisense nucleic acids. The present invention provides the therapeutic or prophylactic use of nucleic acids comprising at least six nucleotides that are antisense to a gene or cDNA encoding an enzyme involved in glucosylceramide synthesis or a portion thereof. As used herein, an "antisense" nucleic acid refers to a nucleic acid capable of hybridizing by virtue of some sequence complementarity to a portion of an RNA (preferably mRNA) encoding an enzyme involved in glucosylceramide synthesis. The antisense nucleic acid may be complementary to a coding and/or noncoding region of an MRNA encoding an enzyme involved in glucosylceramide synthesis. Such antisense nucleic acids have utility as compounds that inhibit expression of an enzyme involved in glucosylceramide synthesis, and can be used in the treatment or prevention of neurological disorder.

The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The invention further provides pharmaceutical compositions comprising a therapeutically effective amount of an antisense nucleic acid which inhibits the expression of an enzyme involved in glucosylceramide synthesis, and a pharmaceutically-acceptable carrier, vehicle or diluent. The antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. The oligonucleotide can be modified at the base moiety, sugar moiety, or phosphate backbone. The oligonucleotide may include other appended groups such as peptides; agents that facilitate transport across the cell membrane (see, e.g., Letsinger et al. (1989) Proc. Natl. Acad. Sci. USA 86:6553–6556; Lemaitre et al. (1987) Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988); hybridization-triggered cleavage agents (see, e.g., Krol et al. (1988) BioTechniques 6:958–976) or intercalating agents (see, e.g., Zon (1988) Pharm. Res. 5:539–549). In a particular aspect of the invention, a antisense oligonucleotide is provided, preferably of single-stranded DNA. The oligonucleotide may be modified at any position on its structure with substituents generally known in the art.

The antisense oligonucleotide may comprise any suitable of the following modified base moieties, e.g., 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, 2,6-diaminopurine, and other base analogs.

In another embodiment, the oligonucleotide comprises at least one modified sugar moiety, e.g., one of the following sugar moieties: arabinose, 2-fluoroarabinose, xylulose, and hexose.

In yet another embodiment, the oligonucleotide comprises at least one of the following modified phosphate backbones: a phosphorothioate, a phosphorodithioate, a phosphoramidothioate, a phosphoramidate, a phosphordiamidate, a methylphosphonate, an alkyl phosphotriester, a formacetal, or an analog of formacetal.

In yet another embodiment, the oligonucleotide is an, α-anomeric oligonucleotide. An, α-anomeric oligonucleotide forms specific double-stranded hybrids with complementary RNA in which, contrary to the usual, β-units, the strands run parallel to each other (Gautier et al. (1987) Nucl. Acids Res. 15:6625–6641).

The oligonucleotide may be conjugated to another molecule, e.g., a peptide, hybridization triggered cross-linking agent, transport agent, or hybridization-triggered cleavage agent.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, and methylphosphonate oligonucleotides can be prepared by use of controlled pore glass polymer supports (Sarin et al. (1988) Proc. Natl. Acad. Sci. USA 85:7448–7451).

In another embodiment, the antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Examples of such promoters are outlined above.

The antisense nucleic acids of the invention comprise a sequence complementary to at least a portion of an RNA transcript of a gene encoding an enzyme involved in glucosylceramide synthesis, preferably a human gene encoding an enzyme involved in glucosylceramide synthesis, however, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1× SSC/ 0.1% SDS at 68° C., or moderately stringent conditions comprising washing in 0.2× SSC/0.1% SDS at 42° C. with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA encoding an enzyme involved in glucosylceramide synthesis it may contain and still form a stable duplex (or triplex, as the case may be). One skilled in the art can ascertain a tolerable degree of mismatch by use of standard procedures to determine the melting point of the hybridized complex.

Pharmaceutical compositions of the invention, comprising an effective amount of an antisense nucleic acid of the invention in a pharmaceutically acceptable carrier, vehicle or diluent can be administered to a subject having neurological disorder. The amount of antisense nucleic acid which will be effective in the treatment of a neurological disorder can be determined by standard clinical techniques.

In a specific embodiment, pharmaceutical compositions comprising one or more antisense nucleic acids to an enzyme involved in glucosylceramide synthesis are administered via liposomes, microparticles, or microcapsules. In various embodiments of the invention, such compositions may be used to achieve sustained release of the antisense nucleic acids.

Inhibitory Ribozyme and Triple Helix Approaches

In another embodiment, symptoms of NPC may be ameliorated by decreasing the level of an enzyme involved in glucosylceramide synthesis by using gene sequences encoding the an enzyme involved in glucosylceramide synthesis in conjunction with well-known gene "knock-out," ribozyme or triple helix methods to decrease gene expression of an enzyme involved in glucosylceramide synthesis. In this approach ribozyme or triple helix molecules are used to modulate the activity, expression or synthesis of the gene encoding the enzyme involved in glucosylceramide synthesis, and thus to ameliorate the symptoms of the disorder. Such molecules may be designed to reduce or inhibit expression of a mutant or non-mutant target gene. Techniques for the production and use of such molecules are well known to those of skill in the art.

Ribozyme molecules designed to catalytically cleave gene mRNA transcripts encoding an enzyme involved in glucosylceramide synthesis can be used to prevent translation of target gene mRNA and, therefore, expression of the gene product. (See, e.g., PCT International Publication WO90/11364, published Oct. 4, 1990; Sarver et al. (1990) Science 247:1222–1225).

Ribozymes are enzymatic RNA molecules capable of catalyzing the specific cleavage of RNA. (For a review, see Rossi (1994) Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy mRNAs encoding an enzyme involved in glucosylceramide synthesis, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers (1995) Molecular Biology and Biotechnology: A Comprehensive Desk Reference, VCH Publishers, New York, (see especially FIG. 4, page 833) and in Haseloff and Gerlach (1988) Nature, 334, 585–591, each of which is incorporated herein by reference in its entirety.

Preferably the ribozyme is engineered so that the cleavage recognition site is located near the 5' end of the mRNA encoding the enzyme involved in glucosylceramide synthesis, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al. (1984) Science, 224, 574–578; Zaug and Cech (1986) Science, 231, 470–475; Zaug, et al. (1986) Nature, 324, 429–433; published International patent application No. WO 88/04300 by University Patents Inc.; Been and Cech (1986) Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the gene encoding the enzyme involved in glucosylceramide synthesis.

As in the antisense approach, the ribozymes can be composed of modified oligonucleotides (e.g., for improved stability, targeting, etc.) and should be delivered to cells that express the enzyme involved in glucosylceramide synthesis in vivo. A preferred method of delivery involves using a DNA construct "encoding" the ribozyme under the control of a strong constitutive pol III or pol II promoter, so that transfected cells will produce sufficient quantities of the ribozyme to destroy endogenous MRNA encoding the enzyme involved in glucosylceramide synthesis and inhibit translation. Because ribozymes, unlike antisense molecules, are catalytic, a lower intracellular concentration is required for efficacy.

Endogenous expression of an enzyme involved in glucosylceramide synthesis can also be reduced by inactivating or "knocking out" the gene encoding an enzyme involved in glucosylceramide synthesis, or the promoter of such a gene, using targeted homologous recombination (e.g., see Smithies et al. 1985) Nature 317:230–234; Thomas and Capecchi (1987) Cell 51:503–512; Thompson et al. (1989) Cell 5:313–321; and Zijlstra et al. (1989) Nature 342:435–438, each of which is incorporated by reference herein in its entirety). For example, a mutant gene encoding a non-functional an enzyme involved in glucosylceramide synthesis (or a completely unrelated DNA sequence) flanked by DNA homologous to the endogenous gene (either the coding regions or regulatory regions of the gene encoding an enzyme involved in glucosylceramide synthesis) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene. However, this approach can be adapted for use in humans provided the recombinant DNA constructs are directly administered or targeted to the required site in vivo using appropriate viral vectors.

Alternatively, the endogenous expression of a gene encoding an enzyme involved in glucosylceramide synthesis can be reduced by targeting deoxyribonucleotide sequences complementary to the regulatory region of the gene (i.e., the gene promoter and/or enhancers) to form triple helical structures that prevent transcription of the gene encoding an enzyme involved in glucosylceramide synthesis in target cells in the body. (See generally, Helene (1991) Anticancer Drug Des. 6(6), 569–584; Helene et al. (1992) Ann. N.Y. Acad. Sci., 660, 27–36; and Maher (1992) Bioassays 14(12), 807–815).

Nucleic acid molecules to be used in triplex helix formation for the inhibition of transcription in the present invention should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

In one embodiment, wherein the antisense, ribozyme, or triple helix molecules described herein are utilized to inhibit mutant gene expression, it is possible that the technique may so efficiently reduce or inhibit the transcription (triple helix) or translation (antisense, ribozyme) of mRNA produced by normal gene alleles of an enzyme involved in glucosylceramide synthesis that the situation may arise wherein the concentration of such an enzyme involved in glucosylceramide synthesis present may be lower than is necessary for a normal phenotype. In such cases, to ensure that substantially normal levels of activity of a gene encoding an enzyme involved in glucosylceramide synthesis are maintained, gene therapy may be used to introduce into cells nucleic acid molecules that encode and express an enzyme involved in glucosylceramide synthesis that exhibit normal gene activity and that do not contain sequences susceptible to whatever antisense, ribozyme, or triple helix treatments are being utilized. Alternatively, in instances whereby the gene encodes an extracellular protein, a normal enzyme can be co-administered in order to maintain the requisite level of activity.

Antisense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Inhibition of Clinical and Pathological Symptoms in a Feline Model of NPC

A domestic cat model of Niemann-Pick C has been described that demonstrates the disorder's characteristic liver storage of cholesterol, glucosylceramide, lactosylceramide and phospholipids, and neuronal storage of GM2 and GM3 gangliosides (Lowenthal et al (1990) *Acta Neuropathol.* (Berl) 81:189–197). A breeding colony for this animal model of NPC is being maintained to study the disease and its potential treatments (Brown et al (1996) *J. Inherit Metab. Dis.* 19:319–330). NPC cats exhibit clinical signs of the disease beginning around 2–3 months with ataxia and titubation, and progress to severe ataxia and death by around 10–12 months.

From seven feline NPC carrier litter mates, normal and NPC-affected male and female cats were selected for the study. The affected female and unaffected male began treatment with NB-DNJ at 1200 mg/kg/day. This administration level proved to be acutely hepatotoxic to the cats, so the treatments quickly had to be ceased. During a brief recovery period for these animals, an unrelated normal cat was treated to determine the maximum tolerated dose for NB-DNJ in this species. Based on this dose-ranging work, the NPC-affected and unaffected litter mates were restarted with NB-DNJ at 50 mg/kg/day. Over the following weeks, the administration level was increased to 150 mg/kg/day. This dose, too, proved to be hepatotoxic, so the administration level was maintained thereafter at 100 mg/kg/day. Except for brief intervals when the treatments were withheld because of transient appetite loss, the NB-DNJ dosages were continued for about three months. On this date, the animals were sacrificed for histologic and lipid analyses.

The following sections highlight the medical and neurologic findings for the study animals.

Cat number: S219; Status: Normal, non-treated; Date of Birth: Nov. 4, 1997; Gender: Male. This cat had an unremarkable developmental course throughout the treatment period, with normal behaviour, mobility and reflexes. He also underwent a normal weight gain, reaching about 3.6 kg by the end of the treatment period. He was not subjected to neurologic assessments during the treatment period.

Cat number: S218; Status: Normal, NB-DNJ-treated; Date of Birth: Nov. 4, 1997; Gender: Female. This cat had an unremarkable developmental course before her treatment period with NB-DNJ began. Her starting dose of 1200 mg/kg/day of NB-DNJ proved to be acutely hepatotoxic, causing a dramatic elevation in her serum levels of liver enzymes. She appeared to fully recover from the hepatotoxicity following a two week non-treatment period, so she was restarted on NB-DNJ at an eventual dosage of 100 mg/kg/day. During the remaining course of the treatment period, she exhibited some symptoms which appeared to be drug-related. Her appetite was significantly less than that of a normal cat, requiring her to be hand-fed during some intervals. Her weight gain reflected her depressed appetite, as she weighed only about 2.4 kg at the end of the treatment period. A normal female cat would be expected to weigh about 4 kg at a similar age. However, while she was exceptionally small for her age, she did not show symptoms of emaciation (e.g. muscle wasting, lethargy). Her hair colour also appeared to be affected by the NB-DNJ treatment. Her fur became markedly more beige than any other cat in the colony during the course of the treatments, even more so than the other NB-DNJ-treated animal (S222, see below). She was not subjected to neurologic assessments during the treatment period.

Cat number: S221; Status: NPC-affected, non-treated; Date of Birth: Nov. 4, 1997; Gender: Male. This cat had an unremarkable developmental course until he began exhibiting the characteristic head tremors and ataxia of feline NPC at about 10 weeks of age. Over the course of the next 20 weeks, his disease symptoms slowly worsened. By the end of the treatment period, he exhibited marked ataxia and head tremors, and required hand-feeding to maintain body weight. The following is a tabulation of his neurologic and medical findings:

| Animal S221 - Affected, non-treated | | | | | |
|---|---|---|---|---|---|
| Week | Front leg Hopping | Rear leg hopping | Vision-menace | Ataxia | Intention Tremors | Weight (gms)* |
| 6.5 | 2 | 2 | 2 | none | None | 544 |
| 12.5 | 2 | 2 | 0.5 | none | Mild | 994 |
| 16 | 2 | 2 | 1 | none | Mild | 1529 |
| 18.5 | 2 | 1.5 | 1 | none | Mod | 1780 |
| 20.5 | 2 | 2 | 2 | mild | Mod | 1906 |
| 22.5 | 2 | 1.5 | 0.5 | mild | Mod | 1990 |
| 24.5 | 2 | 1.5 | 0.5 | — | Mod | 2090 |
| 26.5 | 2 | 1.5 | 0.5 | mod | Mod | 2140 |
| 29 | 2 | 1.5 | 0.5 | mild | Mod | 2270 |
| 30.5 | 1.5 | 1 | 0.5 | mod | Mod | 2337 |
| 32.5 | 2 | 1 | 0.5 | mild | Mod | 2448 |

*measured within 10 days before corresponding neuronal assessment

Cat number: S222; Status: NPC-affected, NB-DNJ-treated; Date of Birth: Nov. 4, 1997; Gender: Female. This cat had an unremarkable developmental course until she began exhibiting the characteristic head tremors and ataxia of feline NPC at about 10 weeks of age. She also was noted to have bilateral luxating patellas at about the same time. As with S218, her starting dose of 1200 mg/kg/day of NB-DNJ was acutely hepatotoxic. After a no-treatment recovery period, her eventual dosage of NB-DNJ at 100 mg/kg/day was reasonably well handled. Her appetite was significantly reduced relative to both normal and NPC-affected cats, requiring her to be hand-fed often. Over the course of the next 20 weeks, her disease symptoms slowly worsened. However, on several occasions it was noted by the consulting neurologist that her symptoms were less severe than those of S221. As with her affected sib, by the end of the protocol she exhibited significant ataxia and head tremors, and she required continual hand-feeding. She too had the light-coloured fur effect of NB-DNJ treatment that was noted for S218. The following is a tabulation of her neurologic and medical findings:

| Animal S222 - Affected, NB-DNJ treated | | | | | |
|---|---|---|---|---|---|
| Week | Front leg Hopping | Rear leg hopping | Vision-Menace | Ataxia | Intention tremors | Weight (gms)* |
| 6.5 | 2 | 2 | 2 | none | none | 522 |
| 12.5 | 2 | 2† | 1 | none | mild | 965 |
| 16 | 2 | 2 | 1 | none | mild | 1265 |
| 18.5 | 2 | 1.5 | 1.5 | none | mild | 1390 |
| 20.5 | 2 | 2 | .5 | none | mod | 1453 |
| 22.5 | 1.5 | 1.5 | 1 | none | mild | 1469 |
| 24.5 | 2 | 2 | 1 | none | mod | 1495 |
| 26.5 | 2 | 1.5 | 1 | none | mild | 1525 |
| 29 | 2 | 1 | 1 | mod | mod | 1565 |
| 30.5 | — | — | 1 | mild | mod | 1590 |
| 32.5 | 1 | 1 | 0.5 | mod | mod | 1677 |

*measured within 10 days before corresponding neuronal assessment
†diagnosed with bilateral luxating patellas Cat number: S161; Status: Normal, NB-DNJ-treated; Date of Birth: Jul. 17, 1995; Gender: Female. This cat, unrelated to the four others in the study, was included in the study to range the maximum tolerated dose of NB-DNJ in this species. Her development was unremarkable at the time when the treatments began, save for the fact that she had a grade 3/4 heart murmur due to valvular insufficiency. She began treatment with 50 mg/kg/day of NB-DNJ on Mar. 15, 1998. Increasing her dose to 200 mg/kg/day brought on symptoms of lethargy, g.i. distress and increased levels of liver enzymes into her serum. Her dosage was decreased to 100 mg/kg/day for the duration of the treatment period. While her appetite and overall responsiveness were decreased at this dose level, her health was sufficiently robust to maintain the treatments. Nonetheless, towards the end of the treatment period, she needed to be hand-fed to maintain her body weight. Thus, NB-DNJ treatment qualitatively delays the symptoms of neurologic degeneration typical for NPC in cats.

Example 2

Histology and Lipid Analysis

The following sections highlight the histologic and lipid analysis findings for the study animals. As with humans, there is an increased expression of gangliosides in feline NPC neurons. Immunocytochemistry demonstrates numerous ganglioside immunoreactive neurons in the cerebral cortex and cerebellum. There is a corresponding increase in neuronal ganglioside level and histology changes seen in NPC humans. Importantly, NPC cats exhibit ectopic dendrite growth similar to that seen in human children with this disease (March et al (1997) Acta Neuropathol. 94:164–172).

Immunocytochemical studies with anti-GM2 ganglioside antibodies were used to probe for ganglioside expression in treated vs. untreated cats in a qualitative manner. Both normal cats, regardless of treatment status, did not display GM2 immunoreactivity in pyramidal cells of the cerebral cortex, Purkinje cells, or cells within the granular layer of the cerebellum. In the NPC cat that was not treated with NB-DNJ, punctate vesicular GM2 labeling was extensive and intensely labelled numerous pyramidal cells of the cerebral cortex which also displayed meganeurites. Also, Purkinje cells of the cerebral cortex and the entire granular cell layer displayed extensive GM2 labelling. In the NPC cat treated with NB-DNJ, GM2 labeling was observed in the cerebral cortex, but was qualitatively less severe compared to the untreated cat. In the cerebellum, the granular cell layer was largely devoid of GM2 immunoreactivity, suggesting that ganglioside storage had been qualitatively diminished relative to that seen in the untreated NPC cat. Purkinje cells also demonstrated qualitatively less GM2 labeling. Thus, NB-DNJ treatment qualitatively decreases the accumulation of glucosylceramide-containing glycolipids (e.g. GM2) typical for NPC in cats.

Example 3

Inhibition of Clinical and Pathological Symptoms in a Mouse Model of NPC

Colonies of mutant mice expressing the NPC phenotype have been described (Pentchev et al., 1984, Miyawaki et al., 1986; Kitagawa, 1987), and has been validated by a number of criteria as an authentic model of the disease (Akaboshi et al., 1997). NPC mice display clinical signs of the disease around 6–8 weeks of age with mild intention tremor and ataxia. By 9 weeks, the mice exhibit severe ataxia, tremors and weight loss. Death results by 10–12 weeks.

The brains of NPC mice are grossly normal. However, microscopic examination reveals swollen somata, meganeurite formation and enlarged axon hillock regions of cortical pyramidal neurons. Meganeurites and neuritic tufts appear in amygdala neuron. White matter and Purkinje cells display axonal spheroids. Anti-ganglioside antibody staining shows increased GM2 levels primarily in laminae II/III and V pyramidal neurons, and astrocytes in layer I. GD2 levels are elevated in pyramidal neurons throughout the cerebral cortex. Moderate increases are also seen for level of GM3 in layer VI, and GM1 in pyramidal neurons. There is no corresponding change in CD3 or asialo-GM2 levels in NPC mouse brains.

Breeding pairs of mice heterozygous for the mutation causing NPC were used to produce offspring that are NPC$^{-/-}$ homozygotes. These animals, along with their normal wild-type littermates, were used in the following NB-DNJ drug study. Where indicated, NB-DNJ was administered daily by mixing with ground mouse chow. Mice were PCR genotyped 2–3 weeks of age to determine their genetic background.

Ten NPC$^{-/-}$ mice, with ages ranging from 3–7 weeks, were entered into a treatment study. Seven were treated with 1200 mg/kg/day and six were untreated. Regardless of treatment, NPC mice between the ages of 0–5 weeks did not display any features of the NPC phenotype. However, by 8 weeks of age, 5 out of 6 untreated NPC$^{-/-}$ mice displayed the clinical phenotype of their disease (intention tremor, ataxia), while none of the NB-DNJ displayed any symptoms of neurologic effects. All six of the untreated mice showed severe neurologic impairment by 9 weeks of age, whereas only 4 of 7 NB-DNJ treated mice displayed any degree of symptoms. By 10 weeks of age, all six untreated NPC$^{-/-}$ mice died or were sacrificed according to veterinary animal care requirements. In contrast, 4 of 7 NPC$^{-/-}$ mice treated with NB-DNJ lived into their twelfth week. Three of these four surviving mice displayed some degree of NPC-induced neural degeneration, while one appeared normal. In this experiment, untreated NPC$^{-/-}$ mice survived 65±1 days (average ±SE; n=6), while NPC$^{-/-}$ mice treated with NB-DNJ at 1200 mg/kg/day survived 88±4 days (n=7). Thus, NB-DNJ treatment increase longevity in NPC mice by 26% in this study, as well as qualitatively delaying the symptoms of neurologic degeneration typical for NPC in mice.

We claim:

1. A method of treating Niemann-Pick type C disease by administration of a therapeutically effective amount of an imino sugar inhibitor of glucosylceramide synthesis.

2. The method of claim 1, wherein the imino sugar inhibitor of glucosylceramide synthesis is an inhibitor of glucosylceramide synthase.

3. The method of claim 1, wherein the imino sugar is selected from the group consisting of N-butyldeoxynojirimycin, N-butyldeoxygalactonojirimycin, and N-nonyldeoxynojirimycin.

4. The method of claim 3, wherein the imino sugar is selected from the group consisting of N-butyldeoxynojiriinycin and N-butyldeoxygalactonojirimycin.

5. The method of claim 1, wherein the imino sugar is administered orally.

* * * * *